Jan. 25, 1955 F. W. ANDERSON Plant Pat. 1,344

NECTARINE TREE

Filed March 29, 1954

WITNESS

Addison E. Avery

INVENTOR

Frederic W. Anderson

Webster & Webster

ATTY

United States Patent Office

Plant Pat. 1,344

Patented Jan. 25, 1955

1,344

NECTARINE TREE

Frederic W. Anderson, Merced, Calif.

Application March 29, 1954, Serial No. 419,631

1 Claim. (Cl. 47—62)

This invention is directed to a new and distinct variety of nectarine tree characterized by yellow-fleshed freestone fruit; the primary object of the invention having been the origination of a nectarine tree bearing fruit, of the type described, which is commercially desirable from the standpoint of its ripening and shipping period.

The instant variety of nectarine tree bears fruit which ripens—desirably—just after the Sungrand nectarine (United States Plant Patent No. 974), and immediately before the Freedom nectarine (United States Plant Patent No. 1161); this being approximately with the Gower nectarine (unpatented); which latter nectarine has long been a standard shipping variety in the State of California.

As compared to the Gower nectarine, the herein claimed nectarine tree bears fruit which is yellow fleshed instead of white; larger by 40% to 50%; better in eating quality; and has good keeping and shipping qualities, being at least as satisfactory as said Gower nectarine.

The present new and distinct variety of nectarine tree was originated by me—as a seedling—in my experimental orchard near Merced, California, during the course of a long and continuing nectarine improvement program; such origination having been accomplished in the following manner:

A considerable number of seeds from a Le Grand nectarine (United States Plant Patent No. 549), produced from a cross made with pollen from an unnamed seedling nectarine that had resulted from a Kim nectarine×Le Grand nectarine F–1 cross, were planted in a nursery row. The Kim nectarine is the subject of United States Plant Patent No. 173.

When the resulting seedlings had reached the height of a foot or so they were top-worked in orchard trees for subsequent observation. At first fruiting most of them were eliminated, but several that evidenced promising characteristics, including the present variety, were retained and further top-worked on other trees. The present variety was selected, after careful and continuing observation of such further top-workings, as being of special value as a commercial variety of nectarine, particularly by reason of its ripening period, as aforesaid.

The asexual reproductions of the instant variety, by top-working, on mature trees in my orchard located as aforesaid have run true in all respects.

Figure 1:
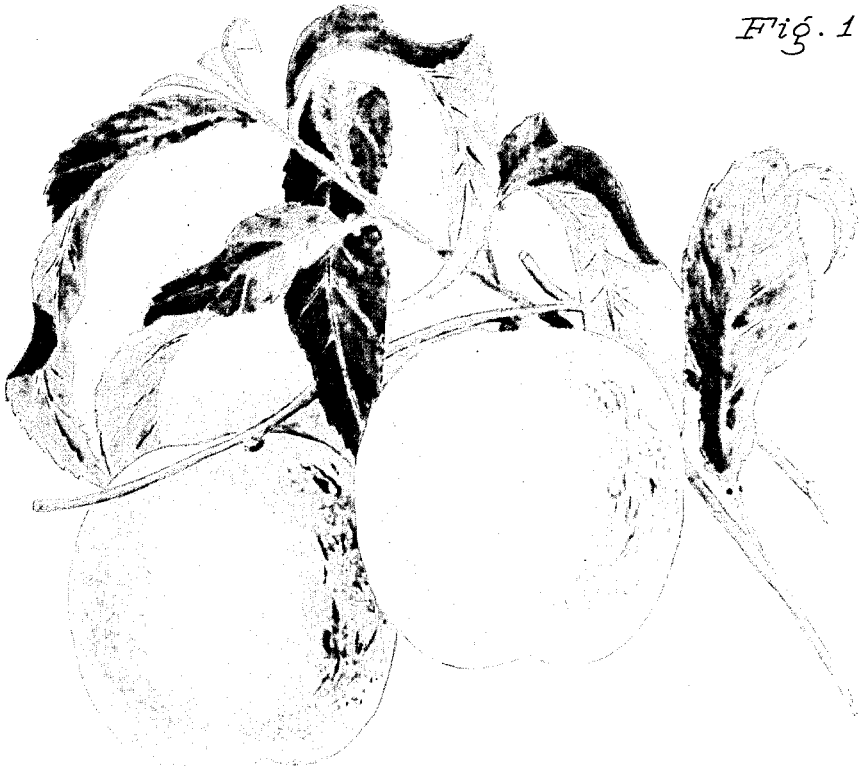
Fig. 1 is an elevation showing two of the fruit of the present variety, together with twigs and leaves.
Figure 2:
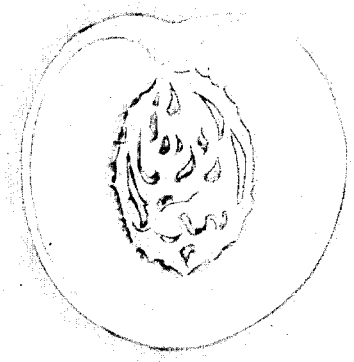
Fig. 2 is a sectional elevation of one of the fruit with the stone exposed.

Referring now more specifically to the pomological details of this new and distinct variety of nectarine tree, the following is an outline description thereof; all major color plate identifications being by reference to Maerz and Paul Dictionary of Color:

Tree: Large; vigorous; upright, spreading; productive; regular bearer.
Trunk: About average in length and stockiness.
Branches: About average in length and stockiness.
*Color.*—Brown.
*Lenticels.*—Medium.
Leaves: Medium to rather large, averaging 6⅜″ in length, and 1⅝″ in width. Ovate. Lanceolate. Medium thickness.
*Color.*—Top side—medium green (21–L–6). Under side—lighter green (21–K–4), with some yellowish shading.
*Margin.*—Crenate.
*Petiole.*—Medium length.
*Glands.*—Usually two, opposite. Medium to small size. Globose. Usually on petiole. No stipules.

Flowers: Large; showy; pink.
*Time of bloom.*—Medium—usually about with the Elberta peach (unpatented).
*Anthers.*—Red, with viable pollen.
Fruit:
*Maturity when described.*—Eating, ripe.
*Date of first picking.*—July 20, 1953.
*Date of last picking.*—July 29, 1953.
*Size.*—Uniform. Large to medium. Well grown specimens average 2¾″ to 3″ in axial diameter, and slightly smaller in cheek-to-cheek diameter.
*Form.*—Uniform. Globose to slightly oblong.
*Suture.*—A shallow line extending from base to beyond, apex, with slight depression beyond pistil point.
*Ventral surface.*—Rounded slightly. Lips equal.
*Cavity.*—Rounded. Circular, averaging about ½″ in depth, and ¾″ in breadth.
*Base.*—Rounded.
*Apex.*—Very short. Slightly depressed.
*Stem.*—Strong, with fruit hanging to tree after ripening.
Skin: Average thickness. Tenacious to flesh. Minimum tendency to crack in humid weather. Down wanting.
*Color.*—Yellow (9–L–5 to 7), closely overlaid or spotted with red (4–J–11), mottled and streaked deeper red (6–L–1).
Flesh:
*Amygdalin.*—Moderate.
*Juice.*—Moderate.
*Texture.*—Firm; meaty.
*Fibers.*—Few.
*Ripens.*—Even.
*Flavor.*—Sub-acid.
*Aroma.*—Distinct, average for yellow varieties of nectarines.
*Eating quality.*—Fair to good.
*Color.*—Yellow (9–K–5) mottled and streaked with red (55–L–1) next to the stone.
Stone: Free.
*Size.*—Large to medium. Average length—1⁷⁄₁₆″. Average breadth—1³⁄₁₆″. Average thickness—1¼″.
*Form.*—Globose to oblong.
*Base.*—Oblique.
*Hilum.*—Broad, oval.
*Apex.*—Acute.
*Sides.*—Somewhat unequal.
*Stone surface.*—Irregularly furrowed and pitted throughout.
*Pits.*—Elongated.
*Ventral edge.*—Thin.
*Dorsal edge.*—Full.
*Ridges.*—Continuous.
*Tendency to split.*—Slight.
*Color.*—Light brown (14–B–11).
Use: Market.
Keeping quality: Good.
Shipping quality: Good.
Resistance to insects and diseases: No unusual susceptibility noted, and the usual spray practices have maintained under control those insects and diseases that are prevalent in the orchard areas of California.

The tree and its fruit herein described may vary in slight detail due to climatic and soil conditions under which the variety may be grown.

Having thus described my invention, I claim:

A new and distinct variety of nectarine tree, as described and illustrated, characterized—as compared to the Gower nectarine—by freestone fruit which is yellow instead of white fleshed, 40% to 50% larger in size, of better eating quality, of equal shipping quality, and having substantially the same ripening period; such period being after the Sun Grand nectarine but before the Freedom nectarine; and further characterized by fruit having a minimum tendency to crack in humid weather, strong stems, and fruit which hangs well on the tree after ripening.

No references cited.